(12) United States Patent     (10) Patent No.: US 8,067,579 B2
Skagestad     (45) Date of Patent: Nov. 29, 2011

(54) NUCLEIC ACID EXTRACTION METHOD

(75) Inventor: Vidar Skagestad, Haslum (NO)

(73) Assignee: Qiagen GmbH, Hilden (DE)

( * ) Notice: Subject to any disclaimer, the term of this patent is extended or adjusted under 35 U.S.C. 154(b) by 225 days.

(21) Appl. No.: 12/307,100

(22) PCT Filed: Jun. 9, 2007

(86) PCT No.: PCT/EP2007/005110
§ 371 (c)(1),
(2), (4) Date: Dec. 30, 2008

(87) PCT Pub. No.: WO2008/000343
PCT Pub. Date: Jan. 3, 2008

(65) Prior Publication Data
US 2009/0192303 A1     Jul. 30, 2009

(30) Foreign Application Priority Data

Jun. 30, 2006    (EP) ..................................... 06013582

(51) Int. Cl.
*C07H 21/00* (2006.01)
(52) U.S. Cl. ...................................................... 536/25.4
(58) Field of Classification Search ........................ None
See application file for complete search history.

(56) References Cited

FOREIGN PATENT DOCUMENTS

WO    WO 02/48164 A2    6/2002
WO    WO 03/091452 A1    11/2003

OTHER PUBLICATIONS

Moret, Inés, et al., "Stability of PEI-DNA and DOTAP-DNA complexes: effect of alkaline pH, heparin and serum," *Journal of Controlled Release* 76:169-181, 2001.

Wahlund, P.-O., et al., "Precipitation by Polycation as Capture Step in Purification of Plasmid DNA From a Clarified Lysate," *Biotechnology and Bioengineering* 87(5):675-684, Sep. 5, 2004.

*Primary Examiner* — Samuel Woolwine
(74) *Attorney, Agent, or Firm* — SEED IP Law Group PLLC

(57) ABSTRACT

The present invention relates to a method for isolating nucleic acids from a nucleic acid containing sample, and a kit for carrying out said method. More specifically, it relates to a novel method for extracting nucleic acids from a nucleic acid containing sample, using an anion exchange solid support, and allowing this solid phase with the nucleic acid bound thereto to react with a compound which is also capable of binding to said anion exchange solid support and which optionally provides additional charges at the surface of the anion exchange solid material, thereby preferably changing the surface charge density of the solid support and then releasing the nucleic acid from the solid support, eliminating the need for high salt and/or high pH elution buffers.

17 Claims, 8 Drawing Sheets

"IE" solid support,
formally positive charge,
neutralized with anionic
counter ions solid support, formally
negative charge,
neutralized with cationic
counter ions Easy binding of NA's Easy elution of NA's

NUCLEIC ACID EXTRACTION METHOD

The present invention relates to a method for isolating nucleic acids from a nucleic acid containing sample, and a kit for carrying out said method. More specifically, it relates to a novel method for extracting nucleic acids from a nucleic acid containing sample, using an anion exchange solid support, and allowing this solid phase with the nucleic acid bound thereto to react with a compound which is also capable of binding to said anion exchange solid support and which optionally provides additional charges at the surface of the anion exchange solid material, thereby preferably changing the surface charge density of the solid support and then releasing the nucleic acid from the solid support, eliminating the need for high salt and/or high pH elution buffers.

Procedures involving nucleic acids (NA's) such as DNA and RNA continue to play a crucial role in biotechnology. Early methods of isolating nucleic acids involved a series of extractions with organic solvents, involving ethanol precipitation (Amersham, U.S. Pat. No. 5,681,946) and dialysis of the nucleic acids. These methods are relatively laborious and often result in low yield.

Later methods take advantage of the fact that nucleic acids are bound to acidic surfaces in the presence of chaotropic salt solutions. This was originally described for diatomaceous earth and for silicon dioxide particles (Boom et al, U.S. Pat. No. 5,234,809). Alternatively, a combination of chaotropes and alcohols can be used (QIAGEN, WO 95/01359). When the chaotropes (and alcohols) are removed from the system, the negatively charged surfaces allow a very easy and efficient elution, that is dissociation of nucleic acids from the solid phase into the water suspension. However, both chaotropes and alcohols are potentially hazardous chemicals that can easily influence down stream analysis, and to some extent reduce the user acceptance of the method.

It is well known that a positively charged solid surface, known in the art as an anion exchange surface, will bind negatively charged species thereto, and the methodology has been used for different purposes. EP 1 404 442 discloses a method to adsorb negatively charged iron oxides (ferrofluids) to positively charged porous surfaces. EP 0 209 251 discloses an IE ("ion exchange") method for protein adsorption to positive charged surfaces, whereas WO 03/074571, US 2002/0025529, and Schmidt et al, J Chromatogr. A. 1999, 865, 27-34 disclose a method for nucleic acid adsorption to a solid support, like plates, columns or beads, wherein said solid support was coated with a polycation.

In comparison to many of the methods using silica and chaotropes ("CS" methods) the use of anion exchange surfaces (abbreviated "IE method") for nucleic acid purification, provides binding in the absence of chaotropes and the use of washing buffers in the absence of chaotropes and/or alcohols, attributing very attractive features to said method. The current limitation of the "IE method", strongly reducing its applicability, relates to elution. The effective adsorption of the negatively charged nucleic acids to the positively charged surface of the ion exchange material hinders an effective elution. In order to overcome these strong interactions between solid support and nucleic acids and to induce the dissociation of nucleic acids from the solid support (=elution), such methods typically utilize elution buffers with high salt concentrations (several Mol) or high pH. For instance, Wahlund et al. disclose in Biotechnology and Bioengineering, Vol 87, No 5, 2004, a method to precipitate plasmid DNA with a solution of poly(dimethyl diallyl ammonium chloride), wherein removal of the polycation from the plasmid was finally carried out using 25 mM Tris, pH 8 containing 2M NaCl.

Moret et al. describe in Journal of Controlled Release, 76, 169-181, 2001, the effect of nucleic acid adsorption to polycations (DOTAP), and how this adsorption protects against nucleases from serum. Release of nucleic acids was carried out using the combined effect of high pH and added heparin.

However, such high salt, high pH or additive conditions are very often in conflict with standard molecular biology down stream analysis (f.e., amplification via PCR), and the isolated nucleic acid therefore needs to be de-salted or the pH must be adjusted prior to further use.

WO 02/48164 discloses the use of "charge switch" material to overcome the necessity of high salt concentrations for efficient elution. The solid phase comprises a positively ionisable nitrogen atom, and at least one electronegative group which is sufficiently close to the nitrogen to lower its pKa value. This surface allows nucleic acid adsorption at a pH below or close to the pKa value. The elution therefore can be carried out at a higher pH. The pH of binding is always lower than the pH of elution. This method has, however, strong limitation in view of the ion exchange surface chemistries to be used, and is therefore by far not particularly useful for those IE solid supports having pka's in the high pH range, which are potentially the strongest (most effective) nucleic acid adsorbers, for instance those surfaces comprising quaternary ammonium ions like —$NR_3^+$. The necessity of a very careful pH control for binding and elution also reduces the general utilisation of said charge switch material.

EP0707077 discloses a synthetic water soluble polymer for precipitation of nucleic acids at acidic pH (pH<7) into a water-insoluble precipitate, and then release of the nucleic acids at alkaline pH (pH>7). Re-dissolving of the polymer-nucleic acid complex is initiated at alkaline pH, elevated temperature and/or high salt concentrations.

In spite of the advantages achieved by the isolation of nucleic acids by means of ion exchange materials, there is still a need for a general method allowing the use of (any) ion exchange material for nucleic acid extraction in combination with a low salt elution.

Thus, the problem of the present invention was to provide a preservative, quick and easy method for nucleic acid extraction providing nucleic acids which immediately can be used in "down stream" methods without the necessity of further treatment steps.

This problem is met by a process for isolating nucleic acid from a nucleic acid containing sample, comprising:
(i) providing a solid phase capable of binding nucleic acids, whereby the solid phase comprises a formally positive or potentially formally positive charge; and
(ii) contacting the nucleic acid containing sample with said solid phase, allowing the nucleic acid(s) to bind to said solid phase; and
(iii) contacting at least one further compound different from the nucleic acid(s), which compound is capable of binding to the remaining formally positive charge on the surface of the solid phase and which optionally changes the charge density on the surface of the solid phase, with said solid phase having the nucleic acid(s) bound thereto, said further compound being not solely $H^+$ or $OH^-$.

One object of this novel method is the combination of the easy binding of nucleic acids with an "IE method" with the easy elution of the same nucleic acids from a formally negatively charged surface which is neutralized with cationic counter ions. Currently in the art, there is a need to choose between said two nucleic acid purification methods.

Surprisingly, it has now been found that such compounds like organic acids which change the surface properties by shielding former formally positive charges are very useful in a "IE method" even when nucleic acids are bound to and eluted from an anion exchange solid support.

By "anion exchange (IE) solid support" according to this invention, a solid support is meant, comprising on its surface either a formally positive charge at all pH-values (typically tertiary or quaternary ammonium salts (—$NHR_2^+X^-$, —$NR_3^+X^-$), or comprising chemical groups which are formally positively charged at a low pH but which show no such formal charge at a high pH (typically primary, secondary and tertiary amines (—$NH_2$, —NHR, —$NR_2$), or comprising a combination thereof. The latter mentioned nitrogen-functionalities therefore can be considered to provide potentially formally positive charges when being protonated. The formally positive charge of the solid support surface typically is neutralized by a counter anion which has a comparatively weak bond strength in comparison to the anions supposed to be bound to the formally positively charged solid support.

The base material of the anion exchange support preferably used for the present invention is of no particular importance as long as it can be provided, preferably on its surface, with a formally positive charge and as long as the base material does not negatively interact with the sample or the chemicals typically used for nucleic acid isolation processes. Common suitable base materials are silica, diatomaceous earth or similar silicon containing compounds or any other materials well known by the skilled person for isolating nucleic acids.

It is particularly preferred to use substances as base material which exhibit magnetic properties when exposed to a magnetic field. Those substances also are well known to the skilled persons.

The anionic exchange materials have the capacity to exchange their counter anion with for instance negatively charged nucleic acids. An example of a corresponding equilibrium using quaternary ammonium ions at the surface of the exchange material is as follows:

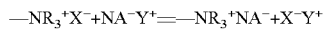

The binding is predominantly reversible and its strength is i.a. determined by the pH and the ionic strength of the solution.

After binding of the nucleic acids to said positively charged surface, the IE material is treated in a way such that the remaining counter ions of the anion exchange material which have not yet been exchanged (at least partly) will be exchanged as well. This is supposed to be achieved by contacting the IE material having the nucleic acids bound thereto with one or more further compounds which should be capable of binding to the positive charge of the IE material with a higher bond strength than the original counter ions but a lower bond strength than the nucleic acids. Thereby, the formally positive charge at the surface of the IE material is supposed to be shielded by the additionally bound compound functioning as the new counter ion.

It is even preferred to use compounds for additionally binding to the exchange material which provide an even higher charge density at the surface of the IE material. "Charge density" generally means the amount of charges in a volume. This increase of the charge density may be achieved by using compounds which have more anionic sites than the ones binding to the exchange material. Thereby, the surface of the IE material originally having formally positive charges may be changed into a surface having a formally negative charge at the outer sphere and the neutralized positive charges below. The additional negative charges at the surface provided by the further compound(s) also are neutralized but by means of a corresponding cationic counter ion. The number of positive and negative charges at the surface of the IE material is thereby increased by the additional positive and negative charges besides the positive and negative charges originally being part of the anion exchange material surface, although the overall sum of the charges is supposed to be neutral.

By this treatment the originally formally positive charge at the surface of the IE material is supposed to be shielded to provide either a neutral outer surface or a neutralized formally negatively charged outer surface.

The "treatment" of the IE solid support after binding the nucleic acids is intended preferably to change the outer charge of the surface of the solid support by "converting" the remaining formally positive charge neutralized by a negative charged counter ion to an additional formally negative charge neutralized by a positive counter ion. This is obtainable by contacting the formally positively charged surface with at least one preferably "charge changing" compound binding or complexing with the positively charged surface and thereby replacing the original anionic counter ion of the IE material. Said compound either renders the surface neutral (the only charge contained in said compound is the one used for binding/complexing) or the compound provides a negative charge to the surface (the compound comprises one or more additional charges besides the charge used for binding/complexing). "Binding" and "complexing" means here the (mainly ionic and/or H-binding) interaction between the nucleic acids and the solid support, or between the further compound(s) and the solid support, respectively.

A "charge changing" compound according to the present invention is any compound which is able to bind via ionic interaction to the solid support of the present invention and which provides an increased charge density, in particular in the form of a formally negatively charged neutralized surface, thereby changing the formal charge of the outer surface, wherein said charge changing compound is not solely $H^+$ or $OH^-$. Preferably the further shielding and optionally charge changing compound(s) according to the invention is at least one acid, most preferred (an) organic acid(s).

Organic acids usable according to this invention are any organic compounds that contain at least one acid functionality, i.e. those which have the ability to undergo dissociation ($RH\rightleftharpoons R^-+H^+$), typically RCOOH, ROH, RSH, $RSO_3H$, and $ROPO_3H_2$ or $(ROPO_2H)_n$. Preferred organic acids usable according to this invention contain more than one identical or different acid functionalities within one molecule, more preferred multiple acid functionalities ("polyacids"). Suitable acids may be comparatively short chain molecules, preferably comprising (denoted as R) from 1 to 26 carbon atoms which may form a straight or branched chain, optionally having each one or more saturated and/or unsaturated sections and which may comprise aliphatic and/or aromatic sections. Moreover, such acids may comprise one or more identical or different acid functionalities like di-, oligo- or polycarboxylic acids, hydroxy carboxylic acids or any other combination of the above defined functionalities. However, it is even more preferred to use organic acids in the form of polymers, for instance like poly(carboxylic acid) such as poly(acrylic acid) or poly(methacrylic acid), poly(sulphonic acid) or poly(alkylphosphoric acid). These organic acids are able to change the formal surface charge of the previous IE solid support from (potentially) positive (=amines, ammonium) into a formally more negative direction (=carboxy $RCO_2^-$, sulphoxy $RSO_x^-$, phosphoric $RPO_x^-$) by providing additional formally negative charges besides neutralizing the former formally positive charges. The polyacids can be of any mass and preferably have a $M_w$ of from 500 to 500.000.

"Mild pH" according to this invention refers typically to a pH<9, preferably in the range of pH 5.5 to 8.5.

By "Low salt" according to this invention is typically meant a liquid/solution/buffer with a salt concentration of 100 mM or lower, preferably of 80 mM or lower, more preferred of 50 mM or lower, most preferred a salt concentration of 30 mM or lower.

Accordingly, in a first aspect, the present invention provides a method for isolating nucleic acids from a nucleic acid-containing sample, which method comprises either:

(a) contacting a formally positively charged or potentially formally positively charged IE solid support with nucleic acids for a time sufficient for binding the nucleic acids to said IE solid support;

(b) contacting the IE solid support, with the nucleic acid bound thereto, with at least one further compound different from the nucleic acid(s), dissolved in water at a pH≦6, which further compound is capable of binding to the remaining formally positive charge on the surface of the IE solid support and which optionally changes the charge density on the surface of the solid support, wherein the compound binds to the solid support; and (c) optionally washing the solid phase with the nucleic acid and the further compound(s) bound thereto; and (d) eluting the nucleic acids from the solid phase at mild pH and low salt conditions;

or:

(e) contacting a formally positively charged or potentially formally positively charged positively charged IE solid support with nucleic acids for a time sufficient for binding the nucleic acids to said IE solid support;

(f) contacting the IE solid support, with the nucleic acid bound thereto, with at least one further compound different from the nucleic acid(s), dissolved in water at a pH>6, which further compound is capable of binding to the remaining formally positive charge on the surface of the IE solid support and which optionally changes the charge density on the surface of the solid support, wherein the compound binds to the solid support; and (g) contacting the IE solid support, with the nucleic acid and the further compound(s) bound thereto, with a liquid comprising an overall pH≦6; and (h) optionally washing the solid phase with the nucleic acid and the further compound(s) bound thereto; and (i) eluting the nucleic acids from the solid phase at mild pH and low salt conditions;

In a second aspect, the present invention provides a kit for isolating nucleic acids from a nucleic acid-containing sample, which kit comprises:

(a) an IE solid support, capable of binding nucleic acid;

(b) optionally a buffer for lysis of a sample;

(c) an aqueous solution of at least one compound capable of binding to the formally positive charge on the surface of the IE solid support and optionally changing the charge density of the surface of the solid support (either pH≦6 or pH>6);

(d) optionally an aqueous solution of pH≦6 (if the aqueous solution of the compound in (c) has pH>6);

(e) optionally a set of washing buffers;

(f) optionally an elution buffer.

In a third aspect, the present invention discloses a method combining the easy binding of nucleic acids in an "IE method", with the easy elution of the same nucleic acids from a formally negatively charged surface which is neutralized with cationic counter ions (FIG. 1), simply by providing the possibility to change/convert the surface nature and charge density of the IE solid support between the binding and the elution of the nucleic acids.

In contrast to what has been possible in the prior art, binding and elution of nucleic acids according to the present invention can now be carried out without changing the pH, and for instance with the same buffers.

In one preferred embodiment of this invention the solid support having the nucleic acid bound thereto is contacted with at least one shielding and optionally charge changing compound as defined above, preferably an organic acid dissolved in water at a pH≦6, more preferably at a pH from 2-5. In order for the compound(s) to bind and interact with the solid support having the nucleic acid bound thereto, and to change the surface charge of the solid support (in a negative direction), it is preferred that the compound(s), preferably the acid(s) is at least in a partially dissociated form, that means partly in the form of $R^-/H^+$. For example an organic acid can be added as a free acid, the corresponding salt, or as a combination thereof.

In an alternative preferred embodiment of this invention the solid support having the nucleic acid bound thereto is contacted with at least one shielding and optionally charge changing compound as defined above, preferably an organic acid dissolved in water at a higher pH (pH>6). Then, the complex of solid support having the nucleic acids and the further compound(s) bound thereto is brought into contact with an acidic liquid at pH≦6 prior to elution. To formulate a liquid solution of pH≦6, as known to those in the art, numerous methods can be used, typically mineral acids, inorganic acids or organic acids (mono-, di or poly acids) or any combination thereof are dissolved, preferably in water, resulting preferably in a pH of from 2-5.

The possible applications for this invention are broad. In the following non limiting example experiments, purification and isolation of nucleic acids (ds DNA, total RNA, ss DNA) from natural samples (like blood, cells, bacteria), or of dissolved (prepurified) samples (like siRNA, tRNA, small fragmented dsDNA) from water are shown. Also included in the experiments are examples of nucleic acid enrichment (siRNA).

In addition, we show that the solid phase of this invention represents an experimental tool to enrich specific components in a biological sample. For example, blood was diluted 50× in an erythrocyte buffer ("red cells lysis only"). The white, non lysed blood cells were adsorbed and enriched (50×) on the IE solid phase of this invention. Thereafter, the gDNa from the cells was isolated by following one of the methods according to this invention with a surprisingly good yield (50% of theoretical amount, based on cell count for whole blood).

Those skilled in the art will therefore realize that the methods according the invention are also very attractive for the enrichment and/or purification of any charged biological species, like for instance viruses, bacteria, organisms, etc from any biological source.

DETAILED DESCRIPTION OF THE INVENTION

As one example of the present invention, IE solid supports comprising $-NR_3^+$ and $-NR_2H^+$ chemical groups were generated. For example, to negatively charged magnetic silica particles (QIAGEN GmbH MagAttract Suspension B, 300 mg/ml) 1% aq poly(ethylene imine) Mw 35.000 or poly(dimethyl diallyl ammonium chloride) Mw 100.000 polymer were added, respectively in water. The former polymer gives a surface chemistry of positive charge at low pH (≦6) ($-NR_2H^+$), and a modest positive charge at high pH (>6)

(—NR$_2$/—NR$_2$H$^+$). The latter polymer, however, shows a permanent positive charge at all pH's (—NR$_3^+$). These solid supports may serve as "typical" IE materials of the present invention, and are fully capable to adsorb nucleic acids under appropriate conditions.

Concerning the binding of the nucleic acids to the IE material, no particular limitations exist. Binding to the solid support can occur at any convenient pH, at any convenient temperature and with any convenient buffer, known by those skilled in the art.

After binding of nucleic acid to the solid support, the same solid support is contacted with at least one shielding and optionally charge changing compound, preferably at least one organic acid that is also capable to bind to the solid support. This will change the surface chemistry of the solid support from a formally cationic, with anionic ions neutralized (prior to nucleic acid binding) to a shielded formally cationic (i.e. having the original anionic ions exchanged without additional anionic functionalities) or preferably to additionally a formally anionic, with cationic ions neutralized (prior to nucleic acid elution) ion exchange solid support.

It is highly preferred to add the shielding and optionally charge changing compound, for example an organic acid, at a proper concentration at this stage. The added solution containing the compound preferably has a concentration of <60% (w/v), preferably from 0.001 to 10% (w/v), more preferred from 0.01 to 2.5% (w/v) of the compound. For example 0.1% of polyacids typically have been found to be sufficient for an efficient adsorption and change of solid support overall surface charge. If an organic acid is added at a high concentration, and even more in combination with a high pH, a not desired elution of the nucleic acids at this stage might occur.

The present invention discloses two alternatives for adding the charge changing compound. In the first embodiment ("one step method", see example 2), said compound, for example an organic acid, is added in the form of a liquid (solution) comprising a pH$\leq$6, either in the form of its acid or its corresponding salt or as a combination thereof, or in the form of a mixture of different organic acids and salts thereof. After one or more optional steps of washing the solid support having the nucleic acids and the shielding and optionally charge changing compound(s) bound thereto, the nucleic acids can be eluted directly by a low salt, mild pH elution solution.

In a second embodiment ("two step method", see example 1), the shielding and optionally charge changing compound, for example at least one organic acid is added in the form of a liquid (solution) comprising a pH>6, in the form of its acid or its corresponding salt, or as a combination thereof, or in the form of a mixture of different organic acids and salts thereof. In order to allow a low salt, mild pH elution, the solid support with the organic acid bound thereto, additionally should be contacted with a liquid having a pH<6.

Several options exist for introducing acidity to the system before elution. A convenient embodiment arises when the acidity is introduced simultaneously with the shielding and optionally charge changing compound, f.e. an organic acid, typically in an aqueous solution comprising a pH$\leq$6, preferably higher than 2, most preferably from 2.5-4.5 (one step method). Those skilled in the art will realize numerous ways to obtain an overall pH less than 6, in particular when an organic acid is present, and the organic acid itself might reduce the pH to pH$\leq$6.

Alternatively, acidity may be introduced after addition of the shielding and optionally charge changing compound such as an organic acid (two step method). In this case the compound is added to the IE solid support having nucleic acid bound thereto, in the form of a solution exhibiting a pH>6. Thereafter, the solid support with the nucleic acid and the shielding and optionally charge changing compound bound thereto, is contacted with a liquid (solution), preferably aqueous, of pH$\leq$6, preferably higher than 2, most preferably from pH 2.5-4.5. One of several possibilities is that the solution for acidification is made of organic acids in which pH is adjusted to <5, preferably higher than 2, most preferably from pH 2.5-4.5, and in which these organic acids preferably are comprised in the form of a polymer, having a buffer capacity. Acidification can be effected directly after adding the charge changing compound, or can be carried out after intermediate washing step(s). However, in order to obtain good results the acidification should occur prior to elution.

Generally in accordance with this invention, and in contrast to for instance the WO 02/48164 case, elution can be carried out at the same or a lower pH than said pH of binding.

Preferably, the elution is carried out with a liquid/solution having a pH in the range of pH 2 to 12, more preferably pH 4 to 10, most preferably pH 5.5 to 8.5.

Moreover, it is particularly preferred to elute the nucleic acid from the solid phase with water or a low salt solution, preferably at a salt concentration <100 mM, more preferably <50 mM, most preferably from >0 to 20 mM.

With respect to the temperature for release, depending on the nature of the nucleic acids elution temperatures from 5 to 95° C. can be employed, although preferably the temperature is in the range of from 20 to 75° C., most preferred at a temperature in which the nucleic acids are not denaturated in any way.

When elution is carried out with a solution of a low pH (pH<7), it can be preferred to additionally apply heat to assist elution. Typically the solution may be heated up to 65° C. In general, the larger the molecular mass of the NA's to be eluted, the higher is the elution efficiency obtained when the pH of the elution buffer is raised, such as to slightly above neutral, for example to pH 8, and when heat is employed. For small nucleic acids like for instance siRNA (21 bp), no effect of heat was observed on the release. Release of total RNA was for instance 2× more efficient at 65° C. compared to at 20° C. in 10 mM Tris pH 8. And release of large gDNA's from human culture cells or blood was even more efficient at elevated temperature.

This invention does not only disclose a method for easy release of nucleic acids from an anion exchange solid material, it also discloses the possibilities to adapt the conditions like salt concentration and/or elution temperature to differentiate between different types of nucleic acids to be eluted.

In addition, this invention discloses a possibility to discriminate the binding of some nucleic acids. For instance, the binding and subsequent isolation of small siRNA (21 bp) from water was strongly reduced in the presence of 20 mM EDTA. For tRNA (70-90 bp), the tolerance for EDTA was much higher. Those skilled in the art will therefore realize numerous ways to discriminate between binding of different length and different types of nucleic acid or other biological components, and to elute them according to this invention.

Skilled persons will also realize this invention to further disclose the possibility for selective isolation of nucleic acid. For instance, adding nucleases will specifically degrade DNA or RNA. Or a high pH in the binding buffer will typically degrade RNA prior to binding.

A preferred embodiment of this invention comprises binding and elution at the same pH, or elution at a lower pH than said pH of binding, however, elution at a pH higher than said pH of binding as well should be regarded as falling under the invention as long as the addition of any charge changing compound is comprised.

The present invention is based on the effect that elution can be well carried out in low salt to no salt buffers/liquids, in contrast to the high salt (typically >1M) buffers currently used in many "IE methods" in the art. Elution performing efficiently from pure water is also possible. It is more convenient for down stream analysis or genetic engineering methods to use a low salt, pH buffered solution. Those skilled in the art will be aware of numerous low salt buffers usable for elution and any following methods. One typical solution usable in molecular biology is 10 mM Tris HCl, pH 8, and this has thus has been used in many of the examples of this application.

The fact that this invention discloses elution at low salt, however, does not, exclude the use of high salts. Elution of nucleic acids from the solid phase of course can also be done at high salt conditions, typically >100 mM.

The nucleic acid-containing samples to be treated according to this invention typically comprise any biological sample such as a cellular sample, cell containing sample or cell fragments containing sample. The biological sample may or may not need to be pretreated, depending on its structure.

The nucleic acid to be isolated may be ss or ds RNA, ss or ds DNA or a modified form thereof. When the nucleic acid is RNA, this preferably may be siRNA, mRNA, total RNA, microRNA, rRNA or tRNA.

This invention is applicable to a wide range of molecular mass nucleic acids. Examples of this application are ranging from ds 21 bp SiRNA to high molecular mass ds gDNA from blood without limiting the invention to these examples.

The chemistry of the IE solid support of this invention has already been addressed. The embodiments of the solid phase include sheets, plates, sieves, sinters, webs and fibres. All these can be part of a handling device, for example a column. However, particles are particularly useful as these may be packed in a column or used in suspension. Magnetic particles are particular beneficial because of the ease with which they merely can be separated from an associated liquid phase in a magnetic field. One type of generally known particles are so called "beads".

The steps of separating the solid phase with the nucleic acid bound thereto from any liquid phase are generally preferred to remove contaminants or undesired residuals in any liquid phase. Any further washing steps with any suitable composition(s) known to those skilled in the art (for instance water, chaotropic solutions, buffers, etc) may be applied to wash the solid phase with the nucleic acid bound thereto. And any convenient separation steps known to those skilled in the art can be utilised in accordance with the present invention.

When for example a magnetic solid phase is used, this facilitates separation, which can be carried out in the presence of a magnetic field. When a membrane or non magnetic particles are used separation may carried out for example by centrifugation.

Depending on the form in which the isolated nucleic acid is desired, any further elution step can be provided. Conditions for elution have already been addressed above.

Without being bound to this theory it is assumed that a main feature of the present invention, i.e. the possibility of low salt release of nucleic acids bound to an IE solid support, is obtained by the following 2 key factors: (1) contacting the IE solid support having the nucleic acid bound thereto with a liquid (solution) of a dissolved shielding and optionally charge changing compound like for example an organic acid, and (2) contacting the IE solid support having the nucleic acid and the shielding/charge changing compound bound thereto with a liquid (solution) having a pH$\leq$6 before eluting the nucleic acid from the IE solid support.

The assumed effect of (1) is to bind and shield the positive surface charge of the solid support so that elution can occur more easily (FIG. 1). Without wishing to be bound to the theory it is speculated that the effect of (2) is to alter and/or support the overall shielding effect. By introducing acidity, the pH of the solution comprising the solid support having the nucleic acid and the shielding and optionally charge changing compound, preferably an organic acid bound thereto, resembles more the pKa of the compound or organic acid added, respectively. That is, a less pronounced dissociation for that compound/organic acid is anticipated. A looser interaction to the IE solid support, or to the nucleic acid bound thereto, is expected, maybe allowing the nucleic acid bound between the solid support and the organic acid to reorganize and release at appropriate elution conditions.

To support the shielding, or in situ surface change idea, following example 1 was repeated in the absence of nucleic acids. After the final elution, the magnetic beads were removed from solution and nucleic acids from water were added. The solid supports had not completely lost their ability to adsorb any nucleic acids.

To verify the advantage of acidification, following example 1 was repeated without any acidification prior to low salt elution. This control experiment didn't allow any recovery of nucleic acids from the eluted buffer.

To verify the advantage of charge changing compounds like organic acids, the following example 1 was repeated without any addition of a charge changing compound. In this control experiment, no change in solid support surface charge occurred, and final elution of nucleic acids was not possible at low salt condition.

FIGURES

Figure 6:
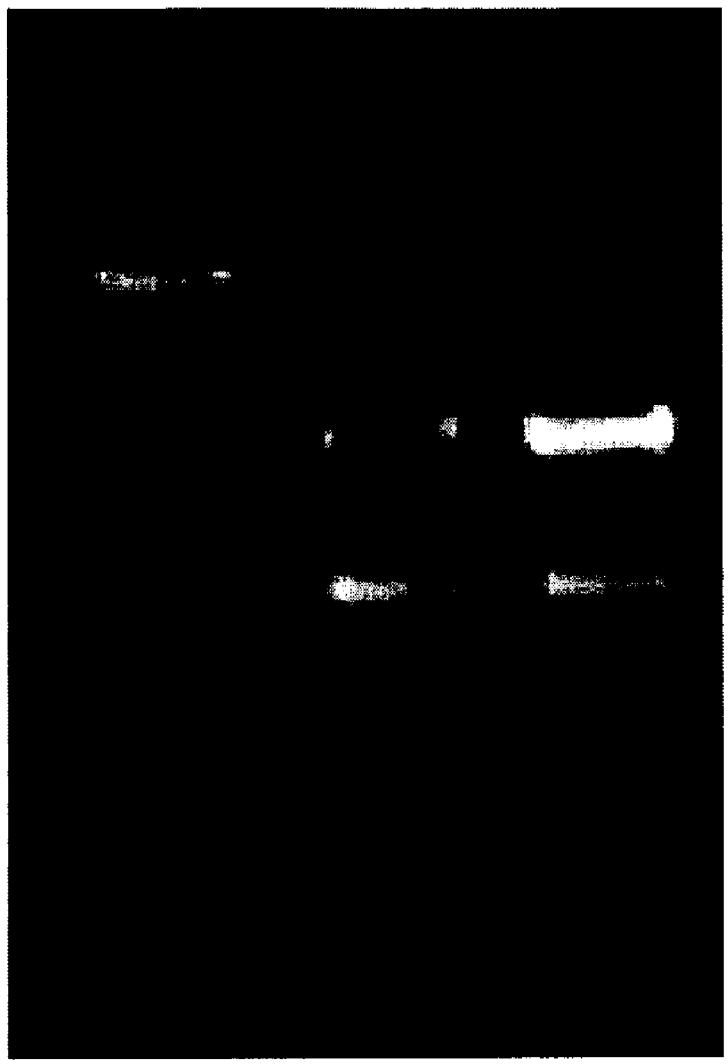

FIG. 6 shows a 1.5% agarose gel comprising isolated nucleic acids from cultured human cells: in lane 1 10 µl isolated RNA, in lane 2 10 µl of the final eluate of nucleic acids eluted at 65° C. and in lane 3 10 µl isolated nucleic acids eluted at 70° C. according to example 9.

Figure 7:
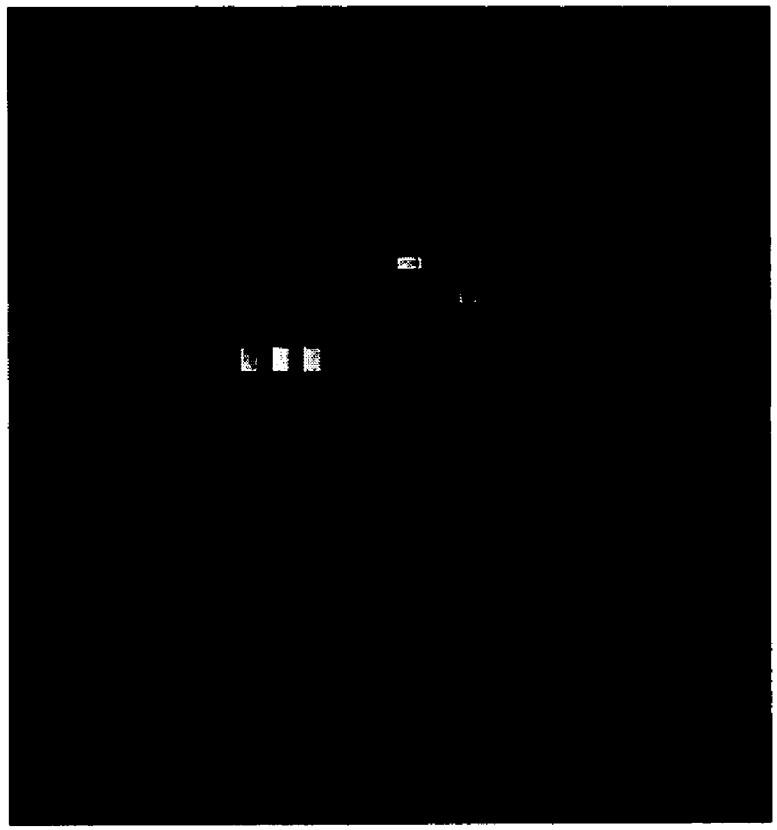

FIG. 7 shows a 1.5% agarose gel comprising 10 µl each of the obtained eluate comprising nucleic acids isolated from (1) 100, (2) 200, and (3) 300 µl E-coli cell suspension according to example 11.

Figure 8:
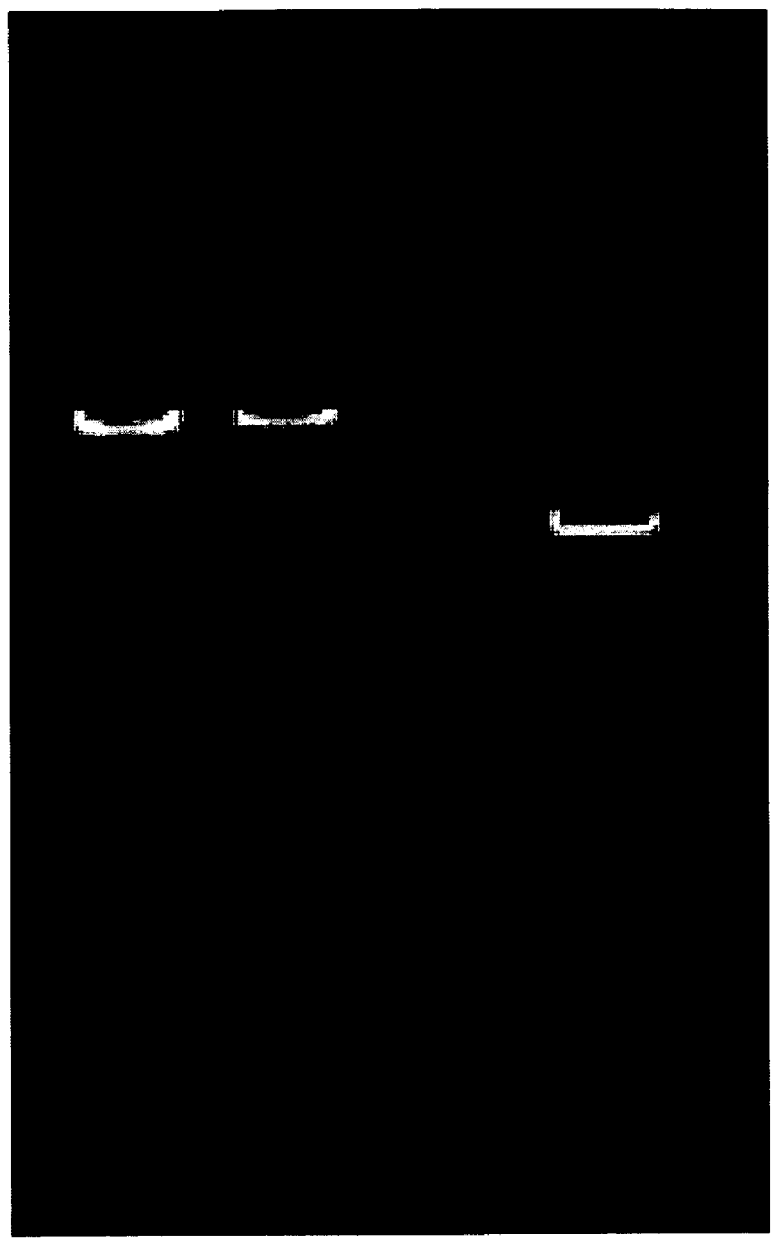

FIG. 8 shows a 0.8% agarose gel comprising in two lanes 10 µl each of the eluate of isolated nucleic acids from tissue prepared according to example 12. In a third lane a 1 kB ladder is shown.

EXAMPLES

Preparation of Solid Phase (A) 1% Poly(ethylene imine), high molecular weight (MW 35.000), water-free, Aldrich, or (B) 1% poly(dimethyl diallyl ammonium chloride), high molecular weight (MW 100.000), Aldrich in water, respectively, were added to 1 ml QIAGEN MagAttract Suspension B magnetic particles (300 mg/ml) each. After incubation for 24 h, the beads were collected on a magnet and the supernatant was removed. Water (10 ml) was added and the beads were incubated for 15 min. The beads were again collected on a magnet and supernatant was removed. This washing procedure was repeated twice. The beads were then stored in different storage media (250 mM LiCl, 100 mM Tris, pH 8, water, 100 mM NaHCO$_3$, pure water) in accordance with the original concentration (300 mg/ml). Any storage media can be used.

As positive control experiments, the beads covered with (A) imine or (B) ammonium (10 μl, 3 mg) were fully capable of adsorbing 5 μg salmon gDNA (Sigma) dissolved in water (100 μl), as it could be expected from positively charged polymer surfaces.

Example 1

Isolation of gDNA from Whole Blood. A Two Step Procedure

200 μl blood (EDTA, cell count of 5.8 mill/ml) were lysed in 600 μl 0.5 M Tris, 1% Triton-100, 2.5% NH$_3$. Lysis was complete within 1 min. 60 μl (18 mg) magnetic solid phase (B) were added to the lysate. After incubation for 10 sec, the magnetic solid phase with the nucleic acid bound thereto, was collected by means of a magnet, and the lysate supernatant was removed. 500 μl of a liquid comprising 0.1% poly(acrylic acid)), Mw 15.000 (Fluka) were then added to the beads in the form of its Na-salt, pH 9.3. After incubation for 10 sec the solid phase was again collected by a magnet, and the supernatant was removed. The procedure was repeated (optional). After removal of the second supernatant an acidified liquid comprising a 1% poly(acrylic acid), Mw 37.000, (Fluka), added to water as the Na-salt, pH adjusted to 3.5 with 37% HCl was added to the magnetic solid phase. The magnetic solid phase was incubated for 10 sec, and the beads were again collected by a magnet, the acidic supernatant was removed and the magnetic solid phase was washed twice with 500 μl water. A final elution in 200 μl 10 mM Tris, pH 8, at 65° C. for 2 min, yielded 6 μg DNA (78% of theoretical amount).

Figure 1:
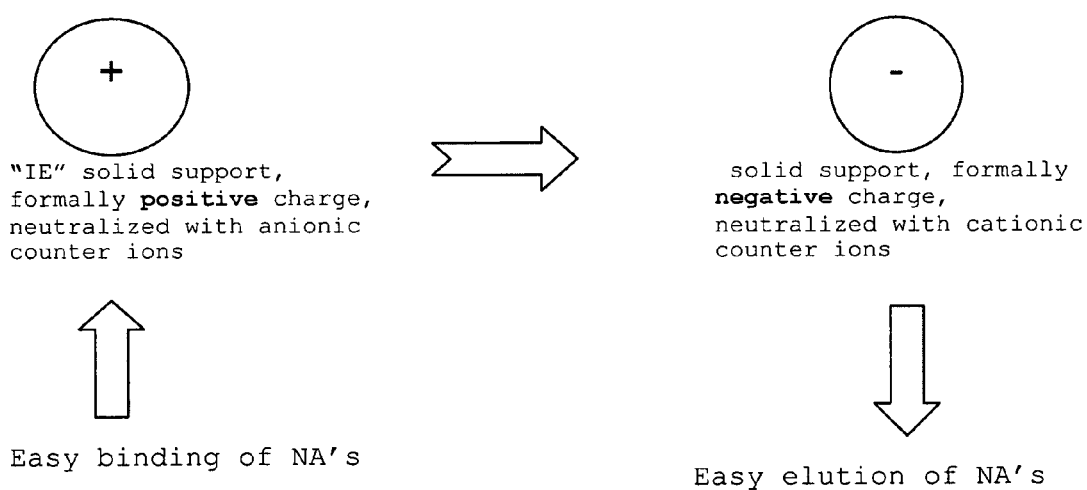
FIG. 1 shows a scheme of the assumed preferred process of the present invention.
Figure 2:
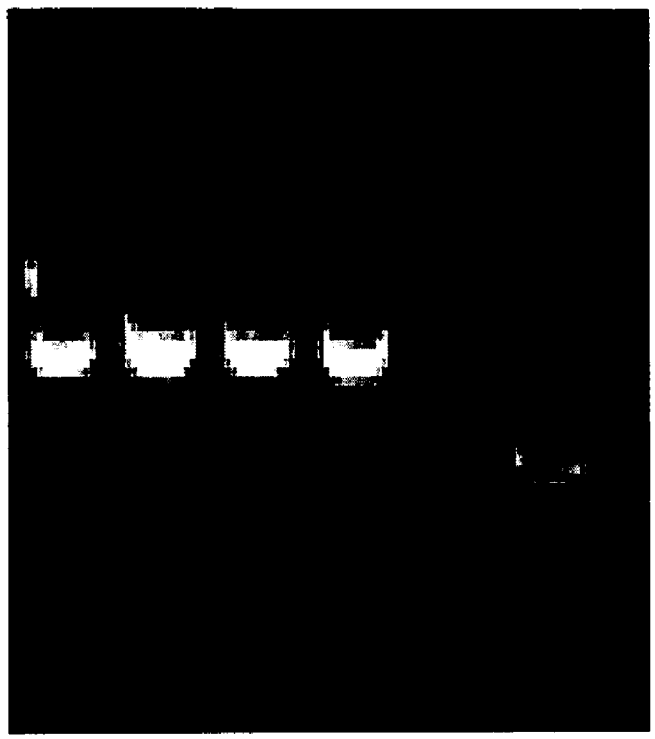
FIG. 2 shows a 0.8% agarose gel comprising in four lanes 10 µl each of the eluate of isolated nucleic acids of whole blood prepared according to example 1. In a fifth lane a 1 kB ladder is shown.
Figure 3:
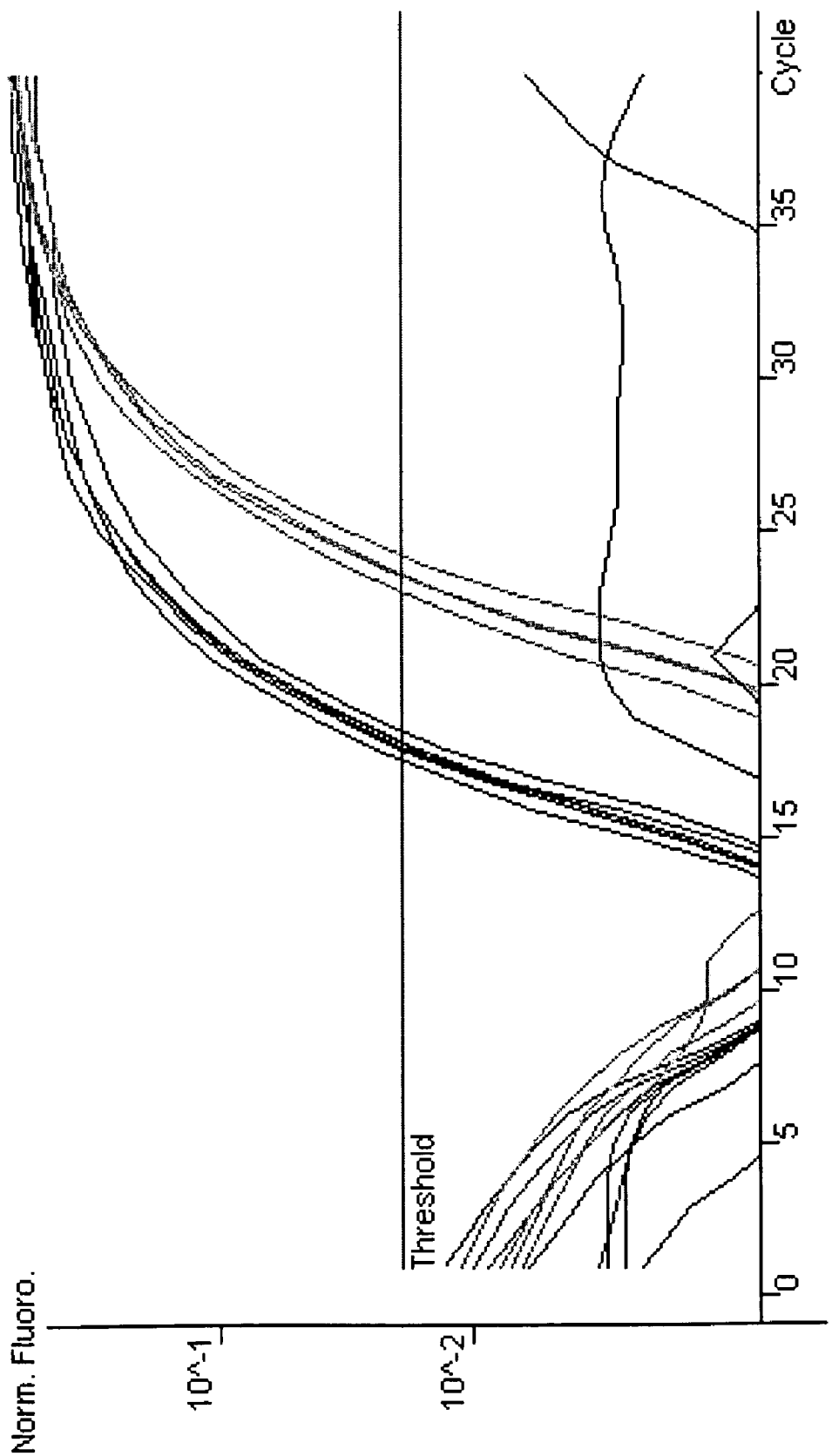
FIG. 3 shows a real time PCR plot of PCR samples prepared with the isolated nucleic acids of example 1.

The isolated DNA (4 parallel lines) was put on an Agarose gel (FIG. 2) (10 μl, 200 ng per line. The gel, 0.8% agarose, shows 4 parallels. On the right is a 1 Kb ladder.), and was amplified according to QIAGEN b-actin QuantiTect RT PCR kit (FIG. 3; 5 μl in a 25 μl PCR mix, positive control also shown).

This example serves to show a two step procedure. The organic acid is added at a high pH (pH>6) to change the overall surface chemistry of the solid phase, with the nucleic acid bound thereto, into a negative direction. Thereafter, a liquid providing acidity (pH<6) is added to the solid phase with nucleic acids and organic acid bound thereto.

Example 2

Isolation of Dissolved (Prepurified) DNA from Sausage. One Step Procedure

200 μl/22 μg fragmented DNA, originally isolated from sausage (with QIAGEN MagAttract Tissue Kit), were dissolved in 200 μl water and 60 μl of ammonium coated beads (B), stored in 100 mM Tris pH 8 were added. After incubation for 10 sec, the beads were collected by a magnet, and the lysate supernatant was removed. The beads were then washed once with 500 μl water. After removal of the supernatant, a 1:1 mixture of 0.1% poly(acrylic acid) Mw 15.000 (Fluka) and 1% poly(acrylic acid) Mw 37.000 (Fluka) was added to the magnetic solid phase with the nucleic acid bound thereto. The pH of the mixture was 4.2. The beads were again collected by means of a magnet, the acidic supernatant comprising the excess of organic acids was removed, and the magnetic solid phase was washed twice with 500 μl water. A final elution in 200 μl 10 mM Tris pH 8 at 65° C., 2 min, yielded 13.6 μg (62% of dissolved material).

Alternatively, after removal of supernatant a 0.1% poly(acrylic) acid Mw 15.000 (Fluka) aq. solution was added at pH 3.5 to the magnetic solid phase with the nucleic acid bound thereto. This gave 13.2 μg DNA.

Figure 4:
FIG. 4 shows a 0.8% agarose gel comprising in three lanes 10 µl each of the eluate of isolated nucleic acids from sausage prepared according to example 2. In a fourth lane a 1 kB ladder is shown.

The isolated DNA (3 parallels) was put on a 0.8% Agarose gel (FIG. 4) (10 μl, 260 ng). The gel shows 3 parallels. On right is a 1 Kb ladder.

This example serves to show a one step procedure. The organic acid solution—either as a mixture of organic acids or as a single organic acid—is introduced in the form of a liquid comprising a low pH (pH<6), to change the overall chemistry of the solid phase with the nucleic acid bound thereto.

Example 3

Figure 5:
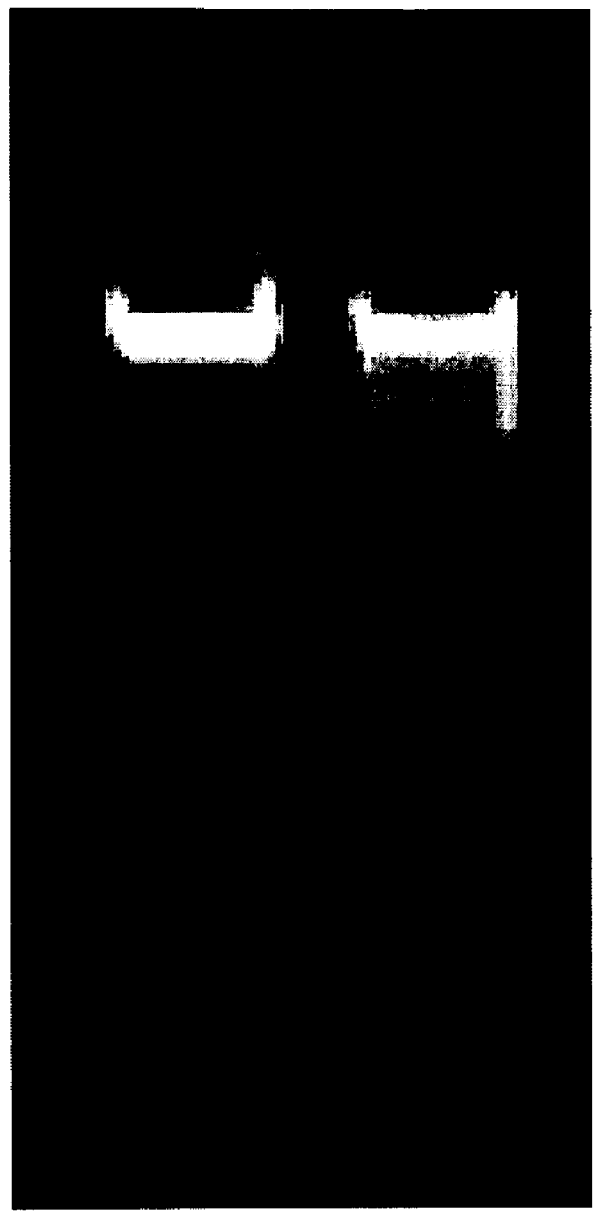
FIG. 5 shows a 0.8% agarose gel comprising in two lanes 10 µl each of the final eluate of isolated nucleic acids from cultured HeLa cells prepared according to example 3.

Isolation of DNA and RNA from HeLa Culture Cells. Effect of a Combined Procedure 1 Million HeLa culture cells were lysed in 400 μl 100 mM Tris, 2.5 mM EDTA, 2.5% Triton-100. To the lysate 60 μl (18 mg) magnetic solid phase (B) were added. After incubation for 10 sec the beads were collected by means of a magnet and the lysate supernatant was removed. The beads were washed once with water and the water phase was removed. To the solid phase, with the nucleic acid bound thereto, first 400 μl 0.1% poly(acrylic acid) Mw 15.000, pH 8.2 in water, and then (after 10 sec) 400 μl 1% poly(acrylic acid) Mw 37.000 (Fluka), pH 3.2 in water were added. The solid phase was incubated for another 10 sec, and the magnetic beads were collected by means of a magnet. The supernatant was removed and the magnetic solid phase was washed twice with 500 μl water. A final elution in 200 μl 10 mM Tris pH 8 at 65° C., 2 min, gave 13.5 μg nucleic acids, as a mixture of DNA and RNA. FIG. 5 shows a 0.8% agarose gel comprising 10 μl of the final eluate in each lane. The gel shows 2 parallels. Mostly DNA is visible.

This example serves to show a mixed procedure of step 1 and step 2. The organic acid (at a pH>6) and an acidic liquid (at a pH<6) can be added subsequently to the solid phase, without any intermediate separation of the solid phase.

Example 4

Isolation of DNA and RNA from HeLa Culture Cells. Effect of Temperature on Final Release 1 Million HeLa culture cells were lysed in 400 μl 100 mM Tris, 5 mM EDTA, 2.5% Triton-100. To the lysate 60 μl (18 mg) of the magnetic solid phase (B) was added. After incubation for 10 sec the beads were collected by means of a magnet, and the lysate supernatant was removed. The beads were washed once with water and the water phase was then removed. To the solid phase, with the nucleic acid bound thereto, first 400 µl 0.1% poly(acrylic acid) Mw 15.000 in water, pH 8.2 (incubation 10 sec) and then 400 µl 1% poly (acrylic acid) Mw 37.000 in water, pH 3.2 (Fluka) were added according to example 2. A final elution in 200 µl 10 mM Tris, pH 8, at RT yielded 14 µg nucleic acids, whereas elution at 65° C., 2 min, yielded 20 µg nucleic acids, as a mixture of DNA and RNA.

This example serves to show the effect of temperature during elution. Although slightly lower efficiency, elution can easily be carried out at RT (15-25° C.).

Example 5

Isolation of Dissolved ds DNA from Salmon. Effect of pH in Final Release

18 µg DNA from Salmon (Sigma) was dissolved in 200 µl 10 mM Tris, pH 8, and isolated according to example 2. In case of elution (65° C., 2 min) was performed in 10 mM Tris, pH 8, the yield was 10 µg. Elution with water (pH ca 4, no neutralization after acidification) gave 6.8 µg DNA.

This example serves to show the effect of pH of the elution buffer. Although slightly lower efficiency, elution can easily be carried out with a liquid having a low pH, for example at a pH much lower than said pH of binding.

Example 6

Isolation of Dissolved DNA. Effect of Length of Organic Acids

28 µg ds DNA (from Salmon, Sigma) was dissolved in 200 µl water and isolated according to example 2. The liquid comprising an organic acid contained:
(a) 10% poly(methacrylic) acid, Mw 4.000, pH 2.5
(b) 10% poly(acrylic acid), Mw 37.000, pH 2.5
(c) 10% poly(acrylic acid), Mw 2.100, pH 2.5

Elution was carried out in 10 mM Tris, pH 8, 65° C., 2 min, and gave (a), 17 µg, (b), 18.4 µg, (c), 18.8 µg.

This example serves to show that a wide range of organic acids can be used in this invention.

Example 7

Isolation of Dissolved tRNA. Effect of pH in the Liquid Comprising the Organic Acid During a One Step Procedure 14 µg tRNA (bovine serum, Sigma) was dissolved in 200 µl water according to example 2. A liquid comprising 0.5% poly(acrylic acid) Mw 100.000 was prepared with different pH values, ranging from 2 to 8. The solid phase, with the nucleic acid bound thereto was exposed to this liquid and the tRNa was eluted according to example 2.

The relative yields of nucleic acids were as follows:
pH 2 (100%), pH 3 (100%), pH 4 (96%), pH 5 (86%), pH 6 (58%), pH 7 (18%), pH 8 (1.5%).

This example serves to show the effect of acidification as a key embodiment. Elution can easily occur when the solid phase, with the nucleic acid bound thereto, is exposed to an acidified liquid, comprising an organic acid at a pH<6.

Example 8

Isolation of Dissolved tRNA. Effect of pH in the Liquid Comprising Acidity During a Two Step Procedure 14 µg tRNA (bovine serum, Sigma) was dissolved in 200 µl water according to example 1. After first being exposed to 0.1% poly(acrylic acid) at pH 9.3, the solid phase with the nucleic acid and the organic acid bound thereto, was exposed to an aqueous solution comprising 0.5% poly(acrylic acid) Mw 100.000 at different pH values, and the tRNA was eluted by 10 mM Tris, pH 8 at RT accordingly.

The relative yields of nucleic acids were as follows:
pH 2 (100%), pH 3 (93%)*, pH 4 (86%), pH 5 (72%), pH 6 (38%), pH 7 (13%), pH 8 (1.3%).
*The experiment for pH 3 was repeated with an aqueous solution acidified with HCl only (no organic acid present). A yield of (82%) was obtained.

This example serves to show the effect of acidification for a two step procedure. Elution can easily be obtained when the solid phase with the nucleic acid and the organic acid bound thereto, is exposed to an acidified liquid, having a pH<6.

Example 9

Isolation of Nucleic Acids from Human Cultured Cells. Effect of Elution Temperature on the Discrimination Between DNA and RNA 250.000 HeLa cells were lysed in 400 µl 100 mM Tris, 10% Triton-100, 25 mM EDTA according to example 1. Nucleic acids were finally eluted by 200 µl 10 mM Tris pH 8 at RT, 65° C., or 70° C. On an Agarose gel shown as FIG. 6 it can be seen that heat elution (line 2, 65° C., 2 min, and in particular line 3, 70° C., 2 min) results in relatively more RNA over DNA in the final elute (line 1 shows RT elution).

This example shows how temperature can effect the release of and discriminate between different types of nucleic acids.

Example 10

Isolation of Nucleic Acids from Human Blood. Enrichment of White Blood Cells Prior to Nucleic Acid Purification 200 µl human blood (cell count 3.8) was dissolved in 10 ml QIAGEN Buffer EL (red cell lysis only). To the 10.2 ml suspension comprising the non lysed white blood cells 200 µl of solid phase (B) were added. After incubation for 5 min, the beads were collected on a magnet, and the supernatant was discharged. The solid phase, with the white cells bound thereto, was lysed in 600 µl 0.5M Tris, 2.5% NH$_3$, 1% Triton-100, pH 10. Following the procedure of example 1, except no addition of extra beads, yielded 2.5 µg DNA (51% based on theoretical amount, OD 260/280 1.74).

This example shows how the IE solid phase of this invention can be used to adsorb and enrich components of biological samples and optionally lyse these and bind nucleic acid thereof.

Example 11

Isolation of Nucleic Acids from E. coli 100 to 300 µl of E-coli in growth media, density OD 0.7, were added to 600 µl 0.5 M Tris, 2.5% NH$_3$, 1% Triton-100, pH 10, and lysed as described in example 1. The nucleic acid was isolated accordingly. The yield was 3.5 µg out of 100 µl E. coli, 6 µg out of 200 µl E. coli and 8 µg out of 300 µl E. coli, OD 260/280 ranging from 2.19 to 2.29

In FIG. 7 the gel shows 10 µl each of the obtained eluate comprising nucleic acids isolated from (1) 100, (2) 200, and (3) 300 µl E-coli on a 1.5% agarose gel.

This example shows the isolation of mainly bRNA from a bacteria sample. However, (some) bDNA+plasmids are also isolated from the E-coli, as seen on top of the gel, in particular on lane 3.

Example 12

Isolation of Nucleic Acids from Tissue 20 mg spleen was dissolved in 600 µl 0.5 M Tris, 2.5% $NH_3$, 1% Triton-100, pH 10. After 10 min at RT, the tissue was physically removed from the lysate, and solid phase as described in example 1 was added to the lysate. The nucleic acid was isolated according to example 1. The yield was 8 µg, OD 260/280 1.91. FIG. 8 shows 10 µl each of 2 parallels of the eluate on an agarose gel.

The gel shows 2 parallels on a 0.8% agarose gel. On right is a 1 Kb ladder. Clear and distinct bands of DNA are visible at the top of the gel. The RNA bands are more degraded (due to degraded RNA from sample, not due to the nucleic acid purification method)

This example shows the isolation of DNA and RNA from a tissue sample.

Example 13

Isolation of Dissolved siRNA

5 µg siRNA (21 bp) was dissolved in 300 µl water, and was reisolated as described in example 2, utilizing a one step procedure with 0.5% poly(acrylic acid), pH 3.5. The recovery after elution in 10 mM Tris, pH 8 at RT, was 3.8 µg (76%), OD 260/280 2.1.

This example shows the isolation of very small ds RNA's.

Example 14

Isolation of Dissolved ds DNA from Salmon

18 µg ds DNA from Sigma was dissolved in 300 µl water and was reisolated as described in examples 2 and 5, utilizing a one step procedure with 0.5% poly(4-styrene sulphonic acid), Mw 3.000 (Fluka), pH 3.2. The recovery after elution in 10 mM Tris, pH 8 at 65° C. was 12 µg (66%), OD 260/280 1.93.

This example shows the use of a sulphonic acid as the charge changing compound.

Example 15

Isolation of Dissolved ds DNA from Salmon using Solid Phase (A)

28 µg ds DNA from Salmon (Sigma) was dissolved in 300 µl water and was reisolated as described in examples 2 or 5, utilizing a one step procedure with the following modifications: 60 µl of magnetic solid phase (A) were added to the dissolved salmon DNA. After binding for 10 sec, the beads were collected by means of a magnet and supernatant discharged. The beads were then washed with 1 M GuHCl (Fluka), followed by 600 µl 10% poly(acrylic acid) Mw 2.100, pH 2.5. After incubation, the solid phase with the nucleic acid and the organic acid bound thereto, was washed with 600 µl 1M GuHCl, and then 2× with 600 µl water. The recovery after elution in 10 mM Tris, pH 8 at 65° C., was 15 µg (53%), OD 260/280 1.93.

This example shows the use of an poly(ethylene imine) solid surface in combination with the use of high salt (chaotrope) washing solutions.

Example 16

Isolation of Dissolved ss DNA from Calf Thymus

16 µg ds DNA, 50 Kb, (from Sigma), was dissolved in 300 µl water and was reisolated either via a two step procedure (as of example 1) or from a one step procedure (as of example 2). The recovery after elution in 10 mM Tris, pH 8.65° C. for 2 min, was 10.0 µg (63%), OD 260/280 1.97, and 10.8 µg (68%), OD 260/280 1.97, respectively.

This example shows equal efficiency of the one step or two step procedure.

Example 17

Control Experiments 1 ml EDTA blood (by "EDTA blood" is meant blood added with EDTA directly after drawn from a human, to avoid coagulation. This is a standard clinical procedure) was lysed with 3 ml 0.5M Tris-HCl, 2.5% $NH_3$, 1% Triton-100, pH 10.0. The 4 ml lysate was then split in 5 equal parts.

In part 1 the nucleic acids were isolated according to example 1, and gave 4.2 µg, OD 260/280 1.80.

In part 2 the nucleic acids were bound to the solid support of example 1, followed by 5 washes with water. Elution according to example 1 gave 0.12 µg, OD 260/280 0.88.

In part 3 the nucleic acids were bound to the solid support of example 1, followed by 5 washes with water. Elution according to example 1 but with 100 mM Tris, pH 12, gave 0.2 µg, OD 260/280 0.84.

In part 4 the nucleic acids were bound to the solid support of example 1 and were treated accordingly, except of acidification. The solid phase with the nucleic acid and the organic acid bound thereto, was washed 3× with 500 µl water. Elution according to example 1 gave 0.68 µg, OD 260/280 1.27.

These comparative examples show the effect of using the key embodiments of this invention, and what happens if any part of them is left out.

The invention claimed is:

1. A process for isolating nucleic acid from a nucleic acid containing sample, comprising: (i) providing a solid phase capable of binding nucleic acids, wherein the solid phase comprises a formally positive charge or a potentially formally positive charge; (ii) contacting the nucleic acid containing sample with said solid phase, allowing the nucleic acid(s) to bind to said solid phase; and (iii) contacting at least one further compound which is capable of binding to the remaining formally positive charges of the solid phase and which optionally changes the charge density at the surface of the solid phase, with said solid phase having the nucleic acid(s) bound thereto, wherein said further compound is an organic acid polymer.

2. The process according to claim 1, wherein the further compound is provided in a solution having pH<6.

3. The process according to claim 1, wherein the further compound is provided in a solution having pH>6, further comprising (iv) contacting the solid phase with the nucleic acid and the further compound bound thereto, to a liquid phase having a pH<6.

4. The process according to claim 1, further comprising a step of eluting the nucleic acid from the solid phase, wherein the elution temperature ranges from 4° C. to 95° C.

5. The process according to claim 4, comprising eluting the nucleic acid from the solid phase with water or salt solution having a salt concentration of 100 mM or lower.

6. The process according to claim 4, wherein elution is carried out with a solution having a pH in the range of pH 2 to 12.

7. The process according to claim 1, wherein the organic acid polymer comprises a free acid, its corresponding salt, or a mixture thereof.

8. The process according to claim 1, wherein the organic acid poles comprises —COOH, —OH, —SH, —OPO$_3$H, or —SO$_3$H chemical group, or a mixture thereof.

9. The process according to claim 1, wherein the organic acid polymer comprises (an) overall mono-, di- or multi-acid functionality (ies).

10. The process according to claim 1, wherein the organic acid polymer has a molecular weight ranging from 500 to 500,000 daltons, and is at a final concentration of less than 60% in the liquid phase.

11. The process according to claim 10, wherein the organic acid polymer is at a final concentration ranging form 0.001% to 10% in the liquid phase.

12. The process according to claim 10, wherein the organic acid polymer is at a final concentration ranging form 0.01% to 2.5% in the liquid phase.

13. The process according to claim 4, wherein the elution temperature ranges from 10° C. to 80° C.

14. The process according to claim 4, wherein the elution temperature ranges from 20° C. to 75° C.

15. The process of claim 5, wherein the low salt solution has a salt concentration less than 100 mM.

16. The process of claim 5, wherein the low salt solution has a salt concentration less than 50 mM.

17. The process of claim 5, wherein the low salt solution has a salt concentration less than 20 mM.

* * * * *

UNITED STATES PATENT AND TRADEMARK OFFICE
CERTIFICATE OF CORRECTION

PATENT NO. : 8,067,579 B2  Page 1 of 1
APPLICATION NO. : 12/307100
DATED : November 29, 2011
INVENTOR(S) : Vidar Skagestad It is certified that error appears in the above-identified patent and that said Letters Patent is hereby corrected as shown below:

Column 17, Line 11:
"acid poles comprises –COOH, -OH, -SH, -OPO$_3$H, or" should read, --acid polymer comprises –COOH, -OH, -SH, -OPO$_3$H, or--.

Signed and Sealed this
Fifteenth Day of May, 2012

David J. Kappos
*Director of the United States Patent and Trademark Office*